United States Patent [19]

Grassmann et al.

[11] Patent Number: 5,424,197
[45] Date of Patent: Jun. 13, 1995

[54] H. SAIMIRI-HTLV-X REGION VECTOR

[75] Inventors: William A. Haseltine, Cambridge; Kathleen McGuire, Jamaica Plain, both of Mass.; Marie-Christine Dokhelar, Paris, France; Ralph Grassmann, Erlangen; Bernard Fleckenstein; Ingrid Muller-Fleckenstein, both of Wiesenthau, all of Germany

[73] Assignees: Dana Farber Cancer Institute, Boston, Mass.; Behringwerke Aktiengesellschaft, Frankfurt, Germany

[21] Appl. No.: 976,661

[22] Filed: Nov. 16, 1992

Related U.S. Application Data

[63] Continuation of Ser. No. 816,774, Jan. 2, 1992, abandoned, which is a continuation of Ser. No. 254,416, Oct. 6, 1988, abandoned.

[51] Int. Cl.$^6$ .................... C12N 15/10; C12N 15/38; C12N 15/48; C12N 15/86
[52] U.S. Cl. ................. 435/69.1; 435/172.2; 435/172.3; 435/240.1; 435/240.2; 435/320.1; 935/32; 935/34; 935/57; 935/71; 935/101; 935/108; 935/109
[58] Field of Search ............. 435/320.1, 172.2, 69.1, 435/240.1, 240.2, 172.3

[56] References Cited

U.S. PATENT DOCUMENTS 4,701,406 10/1987 Chou ..................... 424/3 X
4,981,790 1/1991 Haseltine et al. ............. 435/69.1
5,001,230 3/1991 Brown et al. ............... 536/23.5

OTHER PUBLICATIONS

A. J. Cann, et al., Nature vol. 318. (Dec. 12, 1985) pp. 571–574.
R. C. Desrosiers, Mol & Cell. Biol., vol. 5 (Oct. 1985) pp. 2796–2803.
B. Hallberg, et al., Nucl. Acids Res. vol. 16, No. 13 (Jun. 1988) pp. 5927–5944.
J. D. Rosenblatt, et al., Science vol. 240 (May 13, 1988) pp. 916–919.
Zagury, et al., Science 231:850–853 (1986).
D. V. Faller, et al., J. of Viol. 62:2942–2950 (1988).
A. Derossi, et al., Virology 143:640–645.
I. Miyoshi, et al., Nature 294:770–771 (1981).
N. Yamamoto, et al., Science 217:737–739 (1982).
M. Popovic, et al., Science, 219:856–859 (1983).
V. S. Kalyanraman; et al., Science 218:571 (1982).
I. S. Y. Chien, et al., Nature 305:502 (1983).
E. P. Gelmann, et al., PNAS 81:993 (1984).
M. Seiki, et al., PNAS 80:3618–3622 (1983).
K. Shimotohno, et al., PNAS 81:1079–1083 (1984).
R. Gallo, et al., Nature 333:504 (1988).
M. Hidaka, et al. EMBO Journal 7:519–523 (1988).
K. Shimotohno, et al., PNAS 82:3101–3105 (1985).
J. G. Sodroski, et al. Science 228:1430–1434 (1985).
D. J. Slamon, et al., Science 226:61–65 (1984).
J. G. Sodroski, et al., Science 225:381–385 (1984).
M. Kiyotaki, et al., J. EXPT Medicine 164:926:932 (1986).
D. Celander, et al., Nature 312, 159–162 (1984).
R. C. Desrosiers, et al., J. Virol. 49:343–348 (1984).
R. Grassmann et al. (1989) Proc. Natl. Acad. Sci. USA 86:3351–3355.
B. D. Davis et al., eds. *Microbiology*, 3rd Edition Hagerstown, Md.: Harper and Row, 1980, p. 944.

Primary Examiner—Jacqueline Stone
Assistant Examiner—Johnny F. Railey, II
Attorney, Agent, or Firm—David G. Conlin; Ronald I. Eisenstein

[57] ABSTRACT

An *H. saimiri*-HTLV-1 or 2 X region vector is disclosed. This vector can be used to establish continuous cell lines of difficult to grow cells, such as human T-cells. It can also be used to obtain certain cell products and in methods for screening new compounds.

16 Claims, 6 Drawing Sheets

H. SAIMIRI-HTLV-X REGION VECTOR

This is a continuation of application Ser. No. 07/816,774 filed on Jan. 2, 1992, now abandoned, which is a file wrapper continuation of Ser. No. 07/245,416, filed on Oct. 6, 1988 now abandoned.

The present invention is directed to a vector containing a sequence corresponding to nucleotides of herpesvirus saimiri (*H. saimiri*) and the X-region of human T-cell leukemia virus type 1 or type 2 (HTLV-1 or HTLV-2). This vector can be used to make an immortal cell line of cells that are difficult to cultivate without the presence of feeder cells, a method of making such cell lines, and the products produced by such cell lines. Most preferably, the cells are human T-lymphocytes (T-cells).

Human T-lymphocytes are involved in the regulation of immune reactions by the enhancement or suppression of such reactions and in the destruction of certain autologous cells whose surface characteristics have been altered so that they are no longer recognized by the T-cell as self cells. T-cells carry out these functions, either directly, by cell to cell contact, or indirectly through factors they secrete. These cells also appear to produce regulatory proteins that govern the growth of other cells-particularly of the immune and central nervous system.

These T-cells play an extremely important role in the immune response. Depletion of the CD4+ subset of lymphocytes can account for most of the severe immunologic abnormalities present in patients having the Acquired Immune Deficiency Syndrome (AIDS). This disease is characterized by a long asymptomatic phase followed by the progressive degeneration of the immune system and the central nervous systems. Studies of the virus indicate that replication is highly regulated and both latent and lytic infection of the CD4+ helper subset of T-lymphocytes occur in tissue culture. [Zagury et al, *Science* 231: 850-853 (1986)].

Thus, being able to study T-cells in culture is extremely important, especially with respect to understanding the immune system. However, human T-cells grow very poorly in culture. Specifically, the cytotoxic activity of a primary mixed lymphocyte culture peaks five to seven days after the culture's initiation, declines thereafter and disappears completely at about day ten. In order to return cytotoxic activity, the addition of allogenic cells is necessary. Even such an approach fails after four or five subsequent stimulations. Furthermore, when such cells are diluted in order to obtain pure cultures of specific T-cells, the T-cells will not grow without the presence of other cells, i.e. "feeder cells" such as monocytes, macrophages, dendritic cells or more preferably peritoneal exudate cells.

Faller, D. V. et al. [*J. of Virol.* 62: 2942-2950 (1988)] has reported immortalizing T-cells by infecting them with HTLV-1. However, attempts to use portions of the virus to transform such cells has proven difficult and most, if not all such clones are defective for replication. The pX region of this virus appears particularly important for study as it contains the tax and rex genes among others.

Thus, it would be extremely important to develop a T-cell line that could be continuously or semi-continuously grown without the need for feeder cells or complete viral infection and more preferably, which grow continuously (i.e. an immortalized cell line). Such cell lines could be studied in order to better understand the functioning of T-cells, the factors produced by T-cells, the effect of other compounds on T-cells and could also be used to produce desired proteins. It would also be important if these cells were transformed by the pX region as that region contains genes that effect expression of gene products in trans.

BRIEF DESCRIPTION OF THE INVENTION

We have now discovered a vector comprising a portion of the *Herpesvirus saimiri* genome and also the X-region of the human T-cell leukemia virus type-1 (HTLV-1) or type-2 (HTLV-2). This vector can be used in a method of producing a continuously growing cell line of difficult to grow cells, such as an immortalized T-cell line. This method comprises transforming a cell, for example a lymphocyte with the vector and then culturing the lymphocyte. Such transformed cell lines will continuously grow in standard media, preferably supplemented with Interleukin-2 (IL-2), without complete viral infection or the need for feeder cells.

These immortalized T-cell lines can also be used to express heterologous proteins at high levels such as the IL-2 receptor.

The vector comprises a sufficient number of nucleotides corresponding to the genome of *H. saimiri* to infect a cell but preferably does not contain a sufficient number of the nucleotides of *H. saimiri* which will transform a cell (the *H. saimiri* nucleotides) flanking a sufficient number of nucleotides to transform a cell corresponding to the nucleotides in a 3' region of the genome of HTLV-1 or HTLV-2 designated as pX, a 3' LTR of HTLV-1 or HTLV-2 and a promoter for genes in the pX region collectively referred to as the X region. This X-region segment will not correspond to the entire HTLV-1 or HTLV-2 genome.

This vector can be used in a method of continuously or semi-continuously culturing human cell lines that are difficult to grow, such as T-cells and leukemia cells, without the presence of feeder cells.

BRIEF DESCRIPTION OF THE FIGURES

FIGS. 4A and B are autoradiograms showing the episomal viral DNA persisting in transformed cord blood lymphocytes. FIG. 4A is an ethidium bromide stained gel and FIG. 4B is a Southern blot analysis.

FIGS. 5A-B are autoradiograms showing the HTLV-1 X-region RNA and protein expression in transformed thymocyte lines. FIG. 5A is a Northern blot analysis.

FIG. 6A shows the sequences for HTLV-1 and FIGS. 6B–6C show the sequences for HTLV-2.

DETAILED DESCRIPTION OF THE INVENTION

We have now discovered a vector containing a sufficient number of nucleotides corresponding to a portion of *H. saimiri* genome to infect a cell, and a sufficient number of nucleotides corresponding to the X-region of HTLV-1 or HTLV-2 to transform a cell. The sequence in the vector does not correspond to a portion of the entire HTLV-1 or HTLV-2 genome.

This vector can be used in a method of establishing continuous cell lines of difficult to grow cells, such as human T-lymphocytes without the use of feeder cells or viral infection by a complete virus.

HTLV-1 is a retrovirus which is the etiological agent of adult T-cell leukemia-lymphoma (ATLL), an aggressive neoplasm of CD4+ T-cells. [Potesz, B. J., et al *PNAS* 77: 7415–7419 (1980)]. Tumor cell lines derived from ATLL patients retain many characteristics of the tumor cells themself, including detectable levels of surface CD4 and interleukin-2 receptors. Typically, ATLL derived cell lines also produce HTLV-1 virus particles [DeRossi, A., et al, *Virology* 143: 640–645 (1985)]. Fresh human T-cells may be transformed to permanent growth by being co-cultivated with the virus producing ATLL cell lines and such co-cultivated T-cells closely resemble the tumor cell lines established from patients. [Miyosht, I., et al, *Nature* 294: 770–771 (1981); Yamamoto, N., et al, *Science* 217; 737–739 (1982); Popovic, M., et al, *Science* 219: 856–859 (1983) which are incorporated herein by reference].

HTLV-2 is an isolate originally derived from a patient with a T-cell variant of hairy cell leukemia. [Kalyanraman, V. S., et al, *Science* 218: 571 (1982); Chen, I. S. Y., et al, *Nature* 305: 502 (1983); Gelmann, E. P., et al, *PNAS* 81: 993 (1984) which are incorporated hererin by reference].

The HTLV-1 virus and the HTLV-2 virus both possess genes capable of transforming primary human lymphocytes. Molecular and biochemical studies reveal that, in addition to the genes common to all retroviruses encoding virion structural genes and replicative genes, the genomes of these virus contain an additional segment near the 3′ end. This region termed pX, encodes at least three additional proteins in both viruses. This segment is about 1,600 nucleotides long in HTLV-1. [Seiki, M. et al, *PNAS* 80: 3618–3622 (1983) which is incorporated herein by reference] and 1011 nucleotides long in HTLV-2. The HTLV-2 sequence is very similar to that of HTLV-1 and can be lined up with that of HTLV-1 and is identical at 716 of 1011 nucleotides (70% homology) [Shtmotohno, K., et al, *PNAS* 81: 1079–1083 (1984) which is incorporated herein by reference]. See FIG. 6.

The X regions for both viruses contain a gene that encodes a protein that has a molecular weight of about 42 kD ($p42^{tax}$) in the case of HTLV-1 and about 38 kD ($p38^{tax}$) in HTLV-2. This gene has been named the trans-activator gene (tax) (sometimes previously referred to as $tat_1$ and $tat_2$ or luk or pX or X-lor). These proteins are greater than 90% homologous at the amino acid level and are located predominantly in the nuclei of infected cells. See U.S. Pat. No. 4,738,922 to Haseltine et al filed May 25, 1984. In addition, these retroviruses also contain genes regulating viral protein expression called rex. In HTLV-1, there are two genes, one encoding a protein of 27 kD and the other a protein of 21 kD referred to respectively as $p27^{rex}$ and $p21^{rex}$. [Gallo, R., et al, *Nature* 333: 504 (1988); Hidaka, M., et al, *EMBO Journal* 7: 519–523 (1988) which are incorporated herein by reference]. Similar proteins are encoded by HTLV-2. [Shimotohno, K., et al, *PNAS* 82: 3101–3105 (1985); Rosenblatt, J. D., et al, *Science* 240: 916–919 (1988) which are incorporated herein by reference]. In addition to these genes, the X region also contains other genes.

FIG. 6A is a schematic illustration of HTLV-1 gene expression. The pattern of RNA splicing and coding regions is illustrated, λATK-1 [Seiki et al, *PNAS* 80, supra] is a provtral clone containing cellular flanking sequence (thick bar) at both ends. gag, env and pX represent the corresponding mRNAs. Closed and open triangles on the proviral genome are 5′ and 3′ splice signals; open circle stands for the Sal I site; and open and closed squares stand for the Mlul and Smal sites, respectively. Open boxes over the proviral genome represent coding regions of protein, but do not represent the reading frames.

FIG. 6B is a schematic illustration of HTLV-2 showing the X region. Numbers indicate nucleotides from the 5′ end of the provirus. Bars indicate locations of open reading frames in the genome.

FIG. 6C is a schematic representation of the HTLV-2 genome and coding sequences for certain non-structural proteins. The gag, pol and env coding regions are delineated on the provirus. The boxes above the genome designate coding regions for tax and rex. The 2.1-kb mRNA species schematically illustrated below the HTLV-2 genome contains both tax gene sequences encoding p37, and rex gene sequences encoding the other nonstructural protein(s). The 5′ leader exon (nt 313 to 449), middle exon (nt 5044 to 5183), and third exon (nt 7214 to 8751) are represented by thick lines.

Both tax and rex functions are required for virus replication and it has been proposed that in addition to functions required for such replication, the genes of this region are responsible for the transforming properties of the viruses. [Seiki, M., et al, *PNAS* 80, supra; Sodroski, J. G., et al, *Science* 228: 1430–1434 (1985); Slamon, D. J., et al, *Science* 226: 61–65 (1984); and Sodroski, J. G., et al, *Science* 225: 381–385 (1984)]. However, an examination of the role of the genes in this region in the transformation of primary T-cells has been hampered by the difficulty in establishing cell-free infection with HTLV-1 virus itself because most, if not all, HTLV-1 proviral clones obtained are defective for replication.

The *H. saimiri* is a T-cell tropic herpesvirus of squirrel monkeys. Although not pathogenic for squirrel monkeys, it is potentially oncogenic for several other species of New World monkeys and rabbits where it produces fatal T-cell lymphomas and leukemias. The cells transformed are a restricted CD8+/CD4-lymphocyte subpopulation [Kiyotaki, M., et al, *J. Expt. Medicine* 164: 926–932 (1986)].

Moreover, *H. saimiri* is not known to infect human cells, although indirect evidence indicates that human lymocytes possess a receptor for the virus. [Johnson, D. R., et al, *Intervirology* 13: 21–27 (1980)].

The pX region of HTLV-1 or HTLV-2 is inserted into a plasmid of *H. saimiri.* Preferably, the pX region contains a sufficient deletion from the env region so that functional env protein is not produced. More preferably, the majority of the env gene is deleted. For example, by use of a Sal I to Xho I deletion, which corresponds to nucleotides 5694 to 6518 in HTLV-1 such a deletion can be accomplished. Alternatively, the skilled artisan can chemically synthesize a sequence corresponding to the pX region and omit those nucleotides corresponding to the env region. The nucleotides corresponding to the pX region should include a sufficient number of nucleotides corresponding to the tax and rex regions to encode tax and rex proteins, as well as a long terminal repeat unit (LTR) downstream of this region and a promoter upstream of the tax and rex region. The sequence including the promoter, genes and downstream LTR is collectively referred to as the X region. Preferably, the 3' LTR is the 3' LTR for the respective HTLV used. The promoter used for expression of the HTLV proteins can be any promoter that will permit expression of X region proteins. More preferably, one would use a promoter that is tissue-specific to expression in T-cells, such as the murine retrovirus SL3-3 (the SL3-3 promoter). This promoter directs high levels of RNA and protein synthesis in both murine and human T-cells. [Celander, D. et al, *Nature* 312: 159–162 (1984)]. This promoter is placed 5' to the initiation codons of both the tax and rex genes. Preferably, the X region used is that of HTLV- 1.

Although any *H. saimiri* strain can be used for forming the vector as long as it retains the ability to infect cells, it is preferable to use a strain in which the nucleotides necessary for *H. saimiri* transformation have been deleted, such as strain 11 S4. Preferably the transformation ability is removed by deleting nucleotides corresponding to the left-most end of the L-DNA. The S4 variant of *H. saimiri* strain 11 is lacking 3.5 kb from the left-most L-DNA [Desrosiers, R. C., et al, *J. Virol.* 49: 343–348 (1984)]. See FIG. 1.

The promoter is fused to the X sequence by standard techniques, such as use of an Xho I Hind 3 fragment as disclosed in Celander et al, Nature 312, supra. This fragment can be inserted into nucleotides corresponding to a portion of the *H. saimiri* genome by conventional techniques well known in the art so that the X region sequences are flanked by *H. saimiri* sequences.

For example, the viral DNA of H. saimiri can be co-transfected with a plasmid containing the X region onto a desired cell, such as OMK cells. Transformed cells, containing the virus can be selected by use of a marker, such as resistance to an antibiotic such as G418, and plaques containing the X region DNA can be identified by a marker, such as hybridization with radioactive DNA prepared from the X region by standard techniques. With this method using restriction enzyme and Southern blot analysis, one can determine if the recombinants contain the X region sequences. See FIG. 2. Using antisera to proteins expressed by the X region one can also determine that the recombinants express X region RNA and show rex protein and tax activity by lytic infection of the cells and the addition of the antisera.

These *H. saimiri*-HTLV X region recombinants are then used to transform various cells that are difficult to grow to vitro such as human T-cells and leukemia cells in the absence of feeder cells. Preferably, the cells used are human T-lymphocytes, for example human thymocytes and cord blood cells although other T-cells can be used. Preferably, the cells are stimulated with a lectin such as phytohemagglutinin (PHA) or phorbol ester (PMA) prior to transformation. Thereafter, the cells can be grown in a standard medium, preferably supplemented with IL-2, without the necessity for any feeder cell being present. If a cell is IL-2 dependent it must be grown with IL-2. This condition can readily be determined empirically.

When this vector was used to produce continuous cell lines with thymocyte and cord blood cells, the cultures expressed the T-cell surface markers CD4 and CD5, but not CD8. See FIG. 3. This observation does not exclude the possiblity that the *H. saimiri*-HTLV X region vector may be used to transform cells with a different phenotype at a lower frequency than CD4+ cells or that may grow more slowly than CD4+ cells in mixed culture. In addition, the cell lines can be used to express protein not normally expressed by these cells, such as the receptor for IL-2 as shown by FIG. 4. These cell lines should also express other soluble factors relevant for T-cell regulation, not normally expressed by T-cells. Furthermore, these T-cells can be used in a system for producting a desired product in hill amounts as a result of the presence of the tax and rex genes. Such products include lymphokines, soluble growth factors and also heterologous gene products. The heterologous gene can be introduced to the cell by being part of the *H. saimiri*-HTLV X region vector or by being a part of a different expression vector. Preferably, the heterologous gene is downstream of an HTLV-LTR so that its expression is under the control of the HTLV-LTR. Because the tax gene acts in trans, the heterologous gene product can be produced in high levels as a result of the presence of the tax and rex genes in these transformed cell lines. Thus, these cell lines can readily be used in a method for producing large amounts of a desired protein.

Preferred proteins that these immortal functional T-cells can be used to produce include lymphokines, T-cell specific proteins such as T-cell receptors and growth factors. Furthermore, since the cell lines are continuous, the proteins produced will be of a known specificity. Many of these proteins have useful clinical applications.

In addition to the proteins produced, one can use the T-cells to clone other T-cells which could also be used for therapy or studied to identify various T-cell epitopes.

Furthermore, these cell lines can be used to manufacture specific antibodies to the cells and/or specific antigenic determinants on these cells. This would be done by standard techniques such as injecting the antigenic determinant into another mammal, for example, a rabbit, allowing it to generate more antibodies. Said antibodies can then be prepared by standard techniques.

Furthermore, it is possible to use the vector of the present invention to establish continuous cell lines that produce antibodies to specific antigens. This would comprise taking a biological sample, adding a predetermined antigenic determinant to it and thereafter, determining if an antigen-antibody reaction occurred. For example, by preparing the antigenic determinant from supernatant of a metabolically-labelled cell, one will obtain a labelled antigen. This antigen can be added directly to the biological sample and thereafter, the immunoprecipitates can be resolved by standard techniques, for example, SDS-PAGE, preferably under non-reducing conditions, to determine if there is a reaction. If there is a reaction, the lymphocytes in that predetermined biological sample can then be transformed by standard techniques to an immortal cell line by transfection with the vector of the present invention. The various lymphocytes can then be diluted so that one obtains individual lymphocyte cell lines. Thereafter, by standard techniques, as described above, one can test each cell line, as described above, with the antigen to determine which are producing the desired antibody. Those cell lines can then be further cloned and used to produce the desired antibody. In this manner, one can tailor the antibody wished to be developed so that it is specific to a particular antigen, for example, a cancer cell.

The vector of the present invention can be used to establish various human T-cell clones. Those clones that are immortalized by co-cultivation with HTLV-1 producing cells, retain all of the functional properties of the untransformed cell line, including specific antigen recognition and class II HLA expression. It is expected that the cell lines transformed by the *H. saimiri*-HTLV X region vector will have properties similar to those transformed by the entire virus as shown for primary human lymphocytes [Faller, D. V. et al, *J. of Virol.*, supra].

The transformed cell line, itself, can be used to treat specific illnesses. For example, in patients suffering from certain illnesses where their immune system is not working or where the patient has cancer, the addition of these transformed cell lines can be beneficial.

These cells may also be used to induce tumors in in vivo systems such as in laboratory animals. By innoculating animals with, for example, the transformed T-cells, it will be possible to induce a T-cell malignancy in those animals. These animals can be used in developing a method for screening compounds that are useful for treating the malignancy. For example one can use rabbits to establish a model system for treating human ATLL. One "infects" the laboratory animal with one of these transformed cell lines such as transformed T-cells. Thereafter, one would wait until a tumor developed and then add a predetermined compound to the animal, wait, and determine how the tumor and the animal responded. Alternatively, one could test for compounds that prevent the occurrence of the disease by first adding the predetermined compound such as a vaccine, then innoculating the animal with transformed cell line and waiting to see if the animal becomes infected.

One can also use these immortalized cell lines in vitro to test various compounds on these cell lines and on control cell lines. This could be done by taking a sample containing an immortal cell line and a sample containing another human cell line, adding predetermined substance to each and then determining the reaction of the two cell lines. This type of testing can be done serially or concurrently. Furthermore, various types of drugs can be tested for simply by changing the cell line used, for example using leukemia cells rather than T-cells. Thus this system can be used to develop compounds that will treat ATLL, other T-cell abnormalities, leukemia, etc.

Additionally, it may be possible to use certain of these transformed cell lines as vaccines against ATLL or leukemia. Determining whether a particular cell line produces malignant or attenuated properties of the virus to be treated can readily be determined empirically. Those producing attenuated effects can then be used as a vaccine.

Similarly, these continuous cell lines permit typing of cells, such as leukemias, and research into their mechanism of operation.

The present invention is further illustrated by the following examples. The examples are provided to aid in the understanding of the invention and are not to be construed as a limitation, thereof.

EXAMPLES

A vector of the present invention was prepared by using *H. saimiri* strain 11 S4. The DNA of this strain is about 160 kb and has an internal AT rich (L) region (112 kb). [Bornkamm, G. W., et al, *J. Virol.* 19: 154–161 (1976); Knust, E., et al, *Gene* 25 (1983)] that is flanked at both ends by a non-coding tandemly repeated sequence of high GC contents (H-DNA) [Bankier, A. T., et al, *J. Virol.* 55: 133–139 (1985)]. The S4 variant is lacking 3.5 kb from the left-most L-DNA and is more fully described in Desrosiers, R. C., et al, *J. Virol.* 49: 343–348 (1984). This deleted region is required for tumor formation upon innoculation into animals, but is not required for lytic growth on owl monkey kidney cells (OMK) [Koomey, J. M., et al, *J. Virol.* 50: 662–665 (1984); Desrosiers, R. C., et al, *Science* 228: 184–187 (1985); Desrosiers, R. C., et al, *Mol. Cell. Biol.* 5: 2796–2803 (1985)]. In Desrosier's R. C., et al. *Mol. Cell. Biol.* 5, supra, it was taught that:

A region of the herpesvirus saimiri strain 11 genome has recently been identified that is required for its lymphoma-inducing capacity in vivo and for immortalization of T-cells in vitro; this region of viral DNA is not required for replication of the virus (4, 5, 16). These sequences are located within the first 4.5 kbp of L-DNA at the left H-L-DNA border. This virus does not transform marmoset lymphocytes in cell culture, [Desrosiers, R. C., et al, *J. Virol* 57: 701–705 (1986)], nor does it transform human cells. See FIG. 1.

Figure 1:
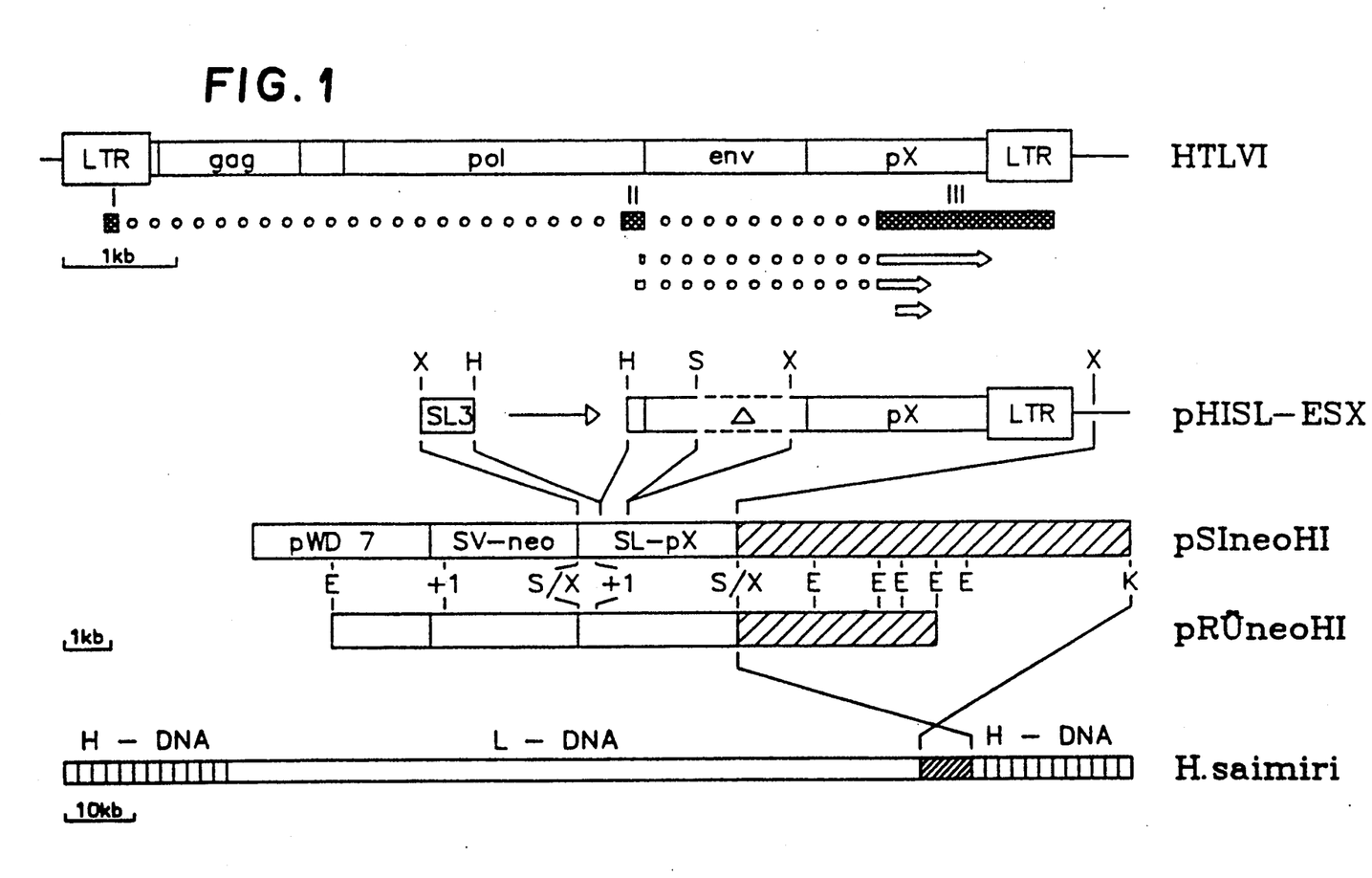
FIG. 1 is a schematic of a plasmid designed for the insertion of the X region of either HTLV-1 or HTLV-2 into the genome of *H. saimiri*. This figure shows the insertion of the X region of HTLV-1.

The X region from HTLV-1 was used. The X region is transcribed into a doubly spliced messenger RNA as described in Aldovtni, A., et al, *PNAS* 83: 38–42 (1986) and Koyotaki, M., et al, *J. Expt. Med.* 164: 926–932 (1986). The region of the HTLV-1 genome used includes nucleotides 5013 to 5694 and nucleotides 6518 to 9054 of the CR provirus. FIG. 1 shows the size and locations of the three exons. This region includes the sequences that encode the amino terminus of the $p42^{tax}$ and $p27^{rex}$ proteins as well as the entire X region and the 3' LTR. The proteins encoded by $p42^{tax}$, $p27^{rex}$ and $p21^{rex}$ are shown as arrows. For expression cloning of the HTLV-1 X region a Hind III (nt 5013) to SacI fragment from a provtral clone described by Manzari, V., et al, *PNAS* 80: 1574–1578 (1983) representing the 3' half of the virus was used. The majority of the env gene was deleted by a SalI (nt 5694) to XhoI (nt 6518) deletion. (Shown as S X in FIG. 1). This HTLV-1 sequence was fused to the SL3-3 muzine retrovirus enhancer promoter [the SL3-3 LTR] contained in a XhoI (X) Hind III (H) fragment, as described by Celander et al, *Nature* 312, supra. The SL3 promoter has been shown to direct high levels of RNA and protein synthesis in murine and human T-cells. The promoter was placed 5' to the initiation codons of both tax and rex.

Prior to the introduction into the *H. saimiri* vector, these HTLV-1 sequences were placed into the plasmids pRUneoH1 and pSIneoH1 so that they were flanked by *H. saimiri* sequences as shown to FIG. 1. These sequences were inserted by using a unique Sal I (S) site of pRUneo and pSIneo, the Sac I(A) site was transformed into a XhoI site by use of T4-DNA-polymerase and linkers. The plasmid SIneo contains the neogene under the transcriptional control of the SV40 early region promoter and the Kpn E fragment originating from the right L-DNA border of *H. saimiri* 11. [See Knust, E., et al, Gene 25, supra]. The plasmid pRUneo is a deletion variant of pSIneo, lacking two EcoRI(E) fragments. Tax activity was shown by using pU3RI-CAT as an indicator.

The viral DNA of *H. saimiri* strain 11 S4 was co-transfected with the HTLV-1X plasmids onto OMK cells by standand technique. Plasmids pSIneoH1 and pRUneoH1 were cut with Kpn I and EcoR I, respectively. Digested plasmid DNA was co-transfected with genomic DNA of *H. saimiri* strain 11 into OMK cells using the calcium-phosphate method at a molar ratio of 80 to 1. See Muesing, M., et al, *Cell* 48: 691 (1987). The resulting viral stocks II (pRUneo) and III (pSIneo) were passaged 3 times on G418-treated OMK cells. Single viral plaques were isolated, expanded and assayed for the presence of heterologous sequences by dot blot anaylsis using radioactive HTLV-1 X region DNA. Viral stocks derived from plaques II-1, II-40 and III-21, III-22 and III-38 were analyzed in closer detail. The radioactive DNA was metabolically labelled by using [$^{35}$S]methionine by standard techniques. Namely, confluent 60 mm plates were labelled 48 hours post-transfection of the HTLV-1 X plasmids with 1.2 ml of methionine-free DME medium containing 1 mCi of [$^{35}$S]methionine (1200 Ci/mmol) for 6 hours.

Figure 2A:
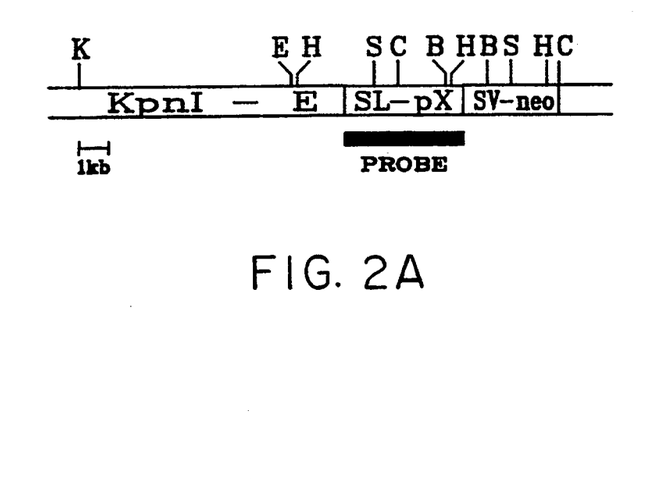
FIG. 2A is a schematic of the arrangement of heterologous sequences in the genome of the recombinants formed. The cleavage sites for EcoRI(E) Cla I(C), Bam HI(B), Kpn I(k) and Sma I(s) are shown.
Figure 2B:
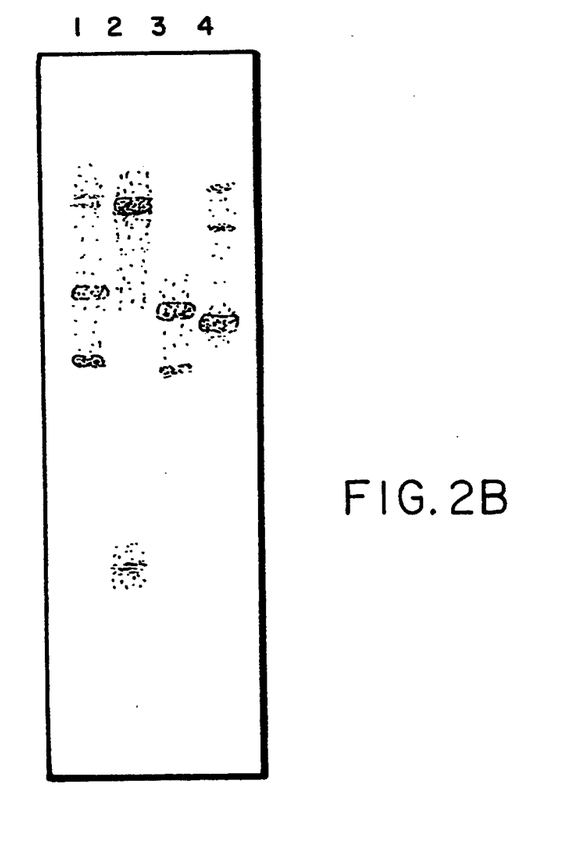
FIG. 2B is an autoradiogram of the *H. saimiri* recombinant SIRpX II-1.

The recombinants were all found to contain the complete HTLV-1 X region sequence by restriction enzyme and Southern blot analysis as seen in FIG. 2. The *H. saimiri* recombinants were shown to express X region RNA and p27$^{rex}$ protein as well as p42$^{tax}$ activity and protein upon lytic infection of OMK cells using anti-sera raised to the nine carboxy terminal amino acids of the p27$^{rex}$ protein and ATLL patient anti-sera, respectively.

FIG. 2A shows the arrangment of heterologous sequences in the genome of the recombinants. The cleavage sites of EcoR1 (E), Cla I (C), Bam HI (B), Kpn I (K) and Sma I (S) are indicated. The bar represents the homology to the hybridization probe used. FIG. 2B shows the Southern blot analysis of the *H. saimiri* recombinant SIRpX II-1. Recombinant viral DNA was digested with EcoR1 and Cla I(1), Kpn I and Bam HI(2), Hind III(3) and Sma I(4), run on a 0.8% agarose gel blotted and hybridized to $^{32}$P-labelled pHISL-ESX. The location of bacteriophage lambda DNA cut with Hind III and of the largest HAE III fragment of PhiX174 are indicated.

Human thymocytes were isolated from a pediatric patient and stimulated with 10 µg/ml phytohemagglutinin (PHA) for 24 hours prior to co-cultivation or "infection." In one experiment, in addition to the PHA 10 ng/ml of phorbol ester (PMA) was also added 24 hours prior to co-cultivation.

These cells were then infected with the *H. saimiri*-HTLV-1 X vector. This was done by washing the vector cells and mixing with the stimulated thymocytes in fresh media containing IL-2 as described in Miyoshi, I. et al, *Nature* 294: 770–771 (1981), Yamamoto, N., et al, *Science* 217: 737–739 (1982) and Popovtc, M., et al, *Science* 219: 856–859 (1983). The cells were split 1:2 every 3 to 4 days to maintain high levels of fresh IL-2. The resulting thymocyte lines were named by the plaque number of the isolated *H. saimiri*-HTLV-1 X vectors responsible for transformation. See FIGS. 3 and 4.

In parallel, thymocyte cells were also co-cultivated with the mitomycin C treated HTLV-1 producing cell lines HUT102 [Poiesz, B. J. et al, *PNAS* 77: 7415–7419 (1980)] and C91PL [Popovic, M., et al, *Science* 219, supra] in the same manner as described above. The cells were washed extensively and mixed with the stimulated thymocytes in fresh media. These cultures were split 1:2 every 3 to 4 days to maintain high levels of fresh IL-2. The resulting thymocyte lines were named for the transforming cell line in the co-cultivation.

In a manner similar to that above, human thymocytes were treated with mitomycin C treated HUT102 and C91PL control cells. These cells were discarded three weeks later because no live cells remain.

The cells were also infected in the manner described above by the *H. saimiri* S4 11 plasmid per se. These cells were discarded after 3 weeks as no cells remained alive.

By contrast, continuous growth of cells with the appearance of lymphocytes were observed in almost all thymus cells treated with the *H. saimiri*-HTLV-1 X vector, as well as in those populations co-cultivated with HTLV-1 producing cells. All the cultures have been maintained for a minimum of 22 weeks post infection.

Figure 3:
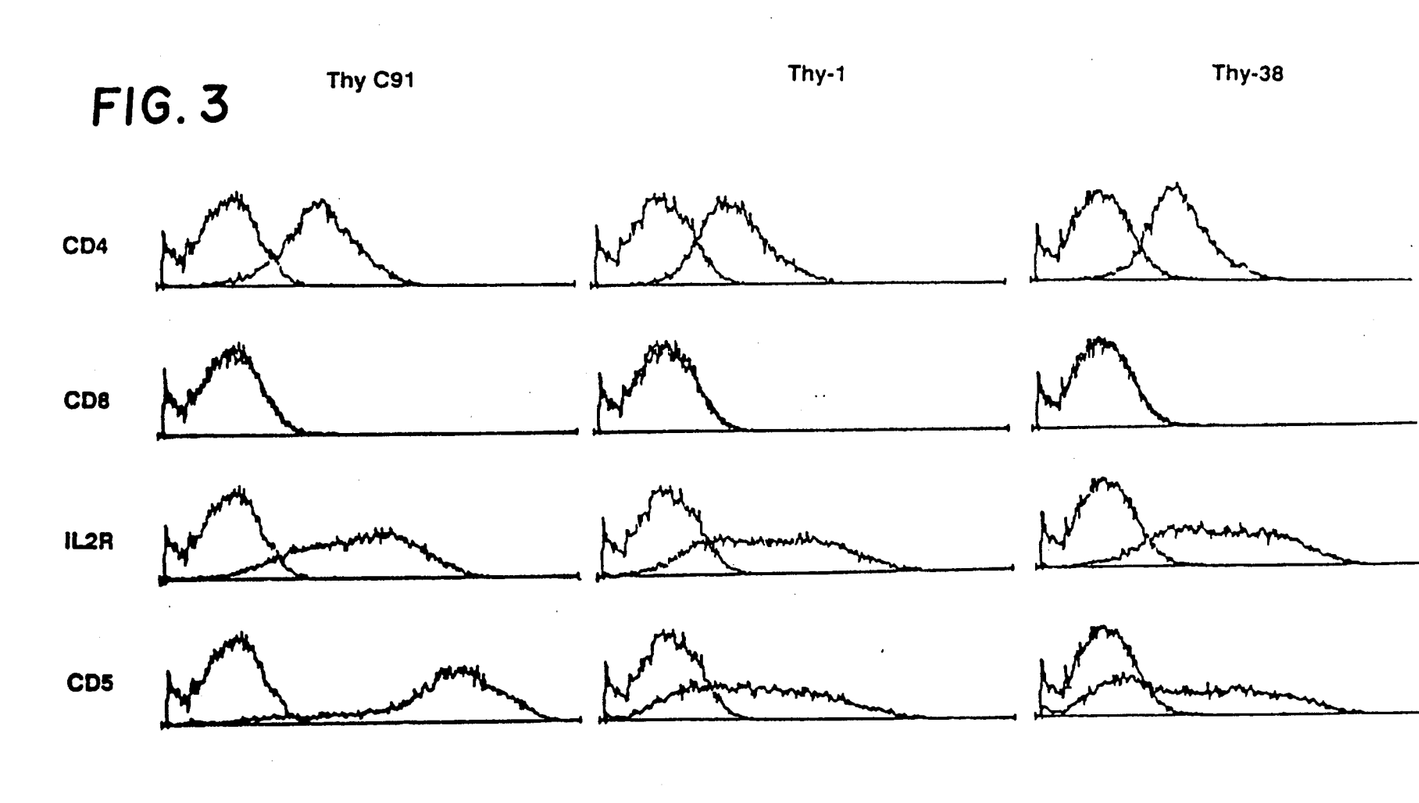
FIG. 3 is a graph showing cell surface expression of T-cell markers in HTLV-1 X-region transformed thymocyte lines.
Figure 4A:
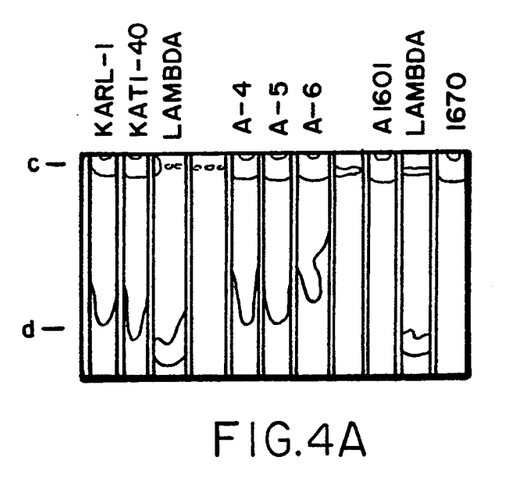
Figure 4B:
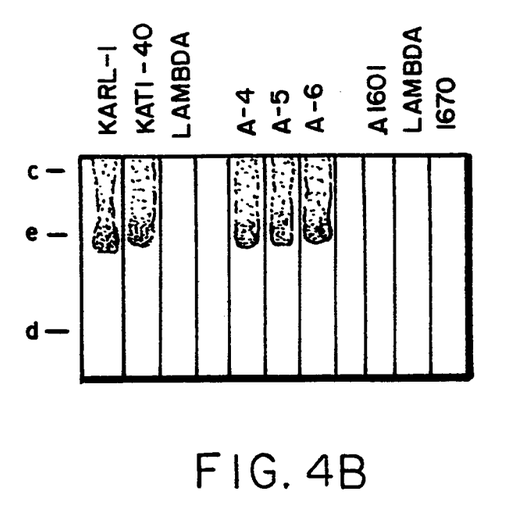

Lymphocyte lines were tested for cell surface expression of the antigens indicated in FIG. 3, using the monoclonal antibodies OKT4 against CD4, OKT8 against CDS, an anti-human IL-2 R α chain monoclonal (T-cell Sciences) and an anti-CD5 monoclonal (Sigma). Fluorescein-conjugated goat anti-mouse immunoglobulin (Ortho Diagnostics) followed by FACS analysis was used to visualize the markers. The fluorescein conjugated antibody alone was the negative control as depicted by the left-most peak in each panel in FIG. 3. Fluorescence intensity is plotted on the abscissa vs. cell number. Thy C91 was derived from a co-cultivation of normal thymocytes with the HTLV-1 infected cell line C91PL. Thy-1 and Thy-38 are two cell lines derived from infection with the claimed vector. Similar results were obtained with two other thymocyte lines, Thy-HUT (See Table 1) and Thy-40. The amount of fluorescence was quantitated using flow cytometry. All cultures were found to express the T-cell surface markers, CD4 and CD5 but were negative for CD8.

Lymphocytes from three different donors were harvested by ficoll-hypaque density gradiant centrifugation and stimulated with PHA as described above. Lymphocytes derived from donor A were depleted of CD8+ cells. Lymphocytes preparations were transformed with the *H. saimiri*-HTLV-1 X vector as described above five days after stimulation and kept in medium containing IL-2. The cell cultures were splits, 1:2 once a week, three weeks after infection. Ten weeks after infection, 1 million cells from continuously growing lymphocyte cultures with virus strains II-1 (Karl-1), II-40 (Kati-40), III-40 (A4), III-22 (A5) and III-38 (A6) were lysed carefully in the slot of a 0.8% agarose gel and subjected to electrophoresis [Gardella, T. et al, *J. Virol.* 50: 248–254 (1984)].

In a similar manner two T-cell lines Fleckenstein, B., et al, The Herpesviruses, pgs 253–332, Plenum Publishing Corp., N.Y. (1982)] containing episomal *H. saimiri* (1670) and H. atelas DNA (A1601) were prepared as controls. Bacteriophage DNA digested with Hind III was used as a size-marker. FIG. 4A is an ethidiumbromide stained gel used to localize the chromosomal DNA (c) and degraded DNA (d). FIG. 4B is a Southern blot analysis. The Gardella type gel (30) was blotted onto a nitrocellulose-membrane and annealed with a radioactive pSV2neo-DNA probe. The position of episomal DNA is indicated (e). Similar results to those shown for the cord blood lymphocyte lines were obtained for the thymocyte lines THY-1, THY-38 and THY-40.

All cultures were found to express the receptor for IL-2 by their reaction with an antibody specific for the 55 kD alpha chain. See third horizontal panel in FIG. 4.

Examination of the thymocyte and cord blood cell lines using Gardella type gels reveals the presence of episomal DNA after in situ lysis of the cells in the well of the gel and also showed that the HTLV-1 X sequence also exists as large episomes (150–200 kb) at high multiplicity (about 100 copies/cell). See FIG. 4. The size and number of genome copies per cell were estimated by comparison with the H. saimiri transformed tumor cell line 1670.

Restriction enzyme digestion followed by Southern blot analysis revealed, intact X region DNA in the thymocyte and cord blood cell lines infected with the H. saimiri-HTLV-1 vectors. Total RNA was extracted from these cultures and analyzed using a radioactive probe to the HTLV-1 X region DNA. RNA was also extracted from HTLV-1 infected cell lines. RNA species corresponding to the full-length transcript, the messenger RNA encoding the envelope glycoprotein and the messenger RNAs corresponding to the tax and rex products were detected as previously reported in the HUT102 cell lines as well as in thymocyte lines derived by co-cultivation with HUT102 and C91PL. See FIG. 5A. [Manzari, V., et al, PNAS 80: 1574–1578 (1983); Franchini, G., et al, PNAS 81: 6207–6211 (1984) and Aldovini, A., et al, PNAS 83: 38–42 (1986)].

Figure 5A:
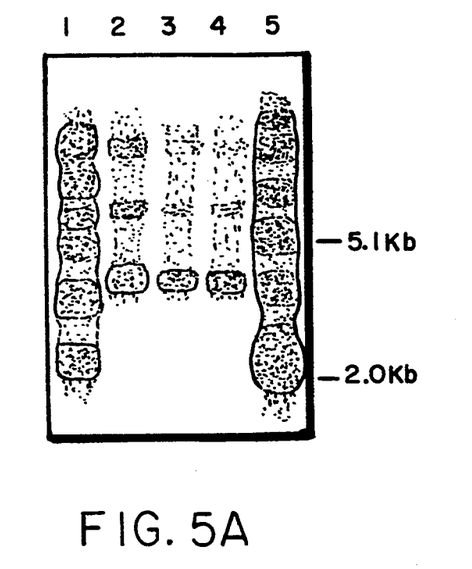

FIG. 5A shows a Northern blot of thymocyte cell lines transformed by the X region of HTLV-1. Twelve weeks post infection, total cellular RNA was isolated and 10 μg of each was electrophoresed in agarose, transferred to Gene Screen Plus and hybridized with a $^{32}$P-labelled probe derived from the X region of the CR HTLV-1 provirus (Acc I-XmaI frag as described by Manzari, V., PNAS 80, supra). The position of the unspliced and spliced X region RNAs are denoted by arrows. Molecular weights were approximated from the position of the 28S and 18S ribosomal RNAs as indicated. Lane 1 is Thy G91, lane 2 THY-40, lane 3 THY-38, lane 4 THY-1, lane 5 HUT102. Results similar to those shown in lanes 2-4 were obtained with the cord blood lymphocyte lines, Karl-1, Kati-40, A4, A5 and A6.

Figure 5B:
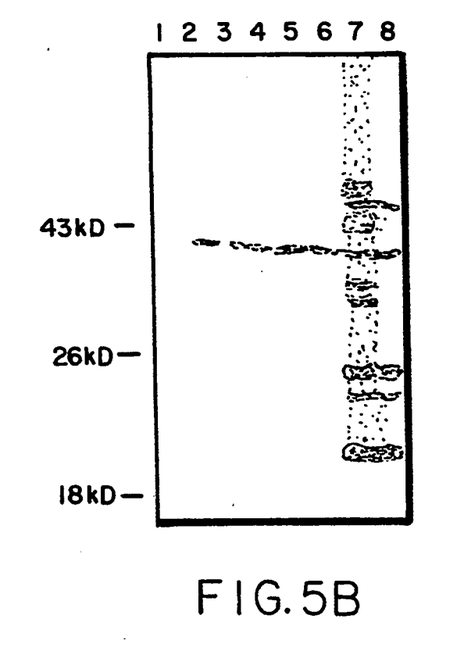
FIG. 5B is a Western blot analysis of p42$^{tax}$ protein expression in transformed thymocyte lines.
Figure 6A:
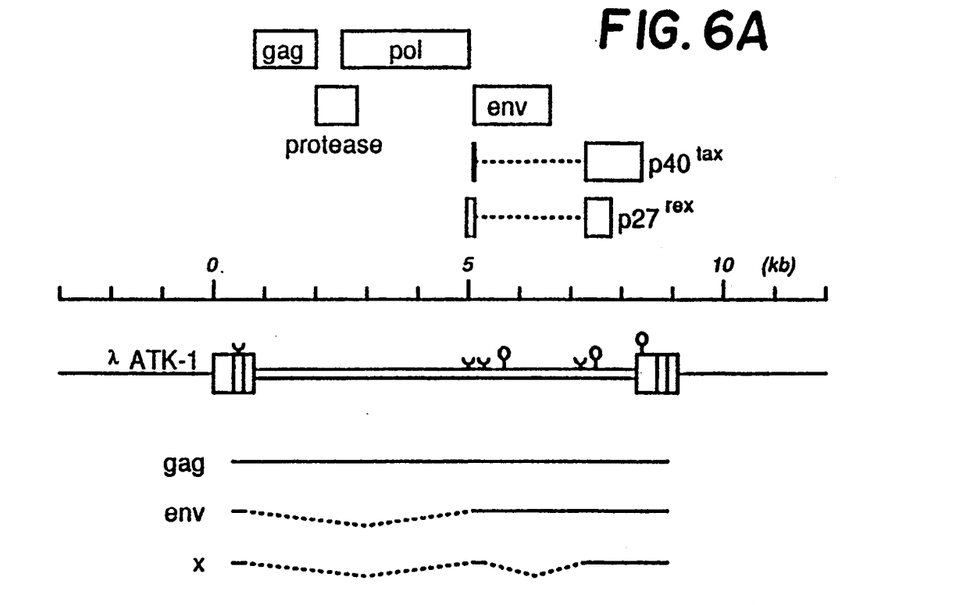
FIGS. 6A-6C are schematics showing the nucleotide sequences of the HTLV-1 and HTLV-2 showing their pX region.
Figure 6B:
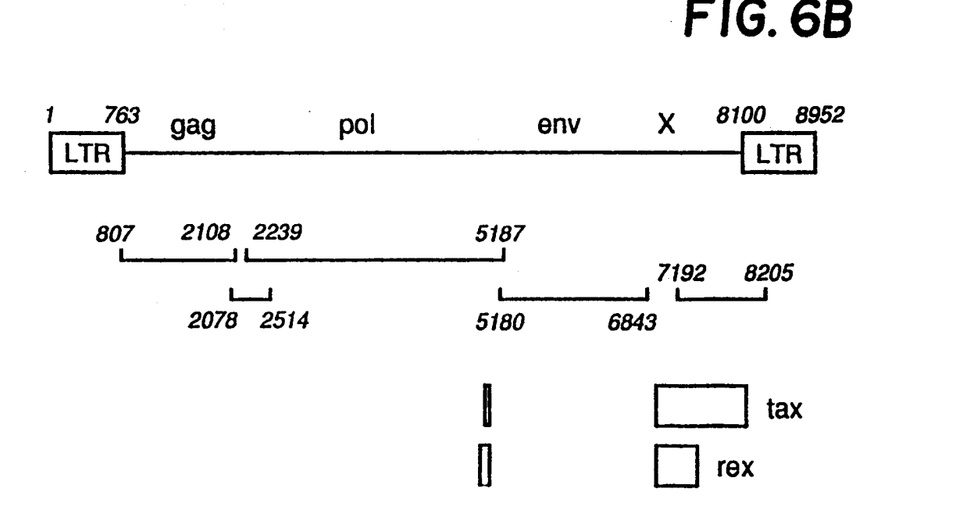
Figure 6C:
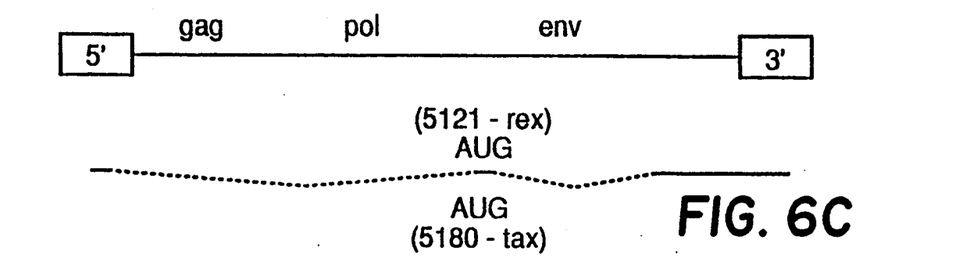

FIG. 5B is a Western blot analysis of p42$^{tax}$ protein expression in the transformed thymocyte lines. $10^6$COS cells were transfected with 5 μg of DNA using DEAE dextran. 48 hours later these cells were lysed and approximately $10^5$ cell equivalents loaded onto a 12% reducing acrylamide gel. In addition, transformed cell lines with the H. saimiri-HTLV-1-X were lysed 14 weeks post-infection and $10^6$ live cell equivalents were loaded and the proteins were electrophoresed and electroblotted onto nitrocellulose. Antiserum from HTLV-1 infected patients was allowed to bind to the filter overnight at room temperature and specific proteins were detected using an alkaline phosphatase conjugated anti-human immunoglobulin and the appropriate substrates (Promega). COS cell controls were transfected with-lane 1 SV$_2$neo, a negative control, lane 2 a tax-producing plasmid, EHX-1, driven by the HIV promoter, lane 3 a tax, rex producing plasmid driven by the HTLV-1 LTR. Infected cell lines were lane 4, THY-1, lane 5 THY-38, lane 6 THY-40, lane 7 C91PL and lane 8 THY-C91.

RNAs of approximately 3.8 kb and 2.0 kb were detected in cells infected with the H. saimiri-HTLV-1-X vectors. These RNA species correspond to the full length transcript initiated within the SL3-3 LTR and the major splice product (denoted by arrows in FIG. 5A). Larger messages probably result from initiation within H. saimiri vector sequences. The ratio of full length transcript to spliced HTLV-1 RNA is approximately 10:1 as determined by densitometry tracing of the audioradiogram.

The tax product detected using ATLL patient antiserum (See FIG. 5B) was active. This was determined by transfecting several of the H. saimiri-HTLV-1-X transformants and the cultures co-cultivated with HTLV-1 cells with the indicator plasmid pU3R1-CAT [Sodroski, J. G., et al, Science 225: 381–385 (1984)] which contains the HTLV-1 LTR located 5' to the bacterial gene for chloramphentcol acetyl transferase (CAT). The relative activity of the pU3R1-CAT and pRSV-CAT plasmids were determined in the Jurkat T-cell line that does not contain HTLV-1 sequences. The result of the experiment summarized In Table 1 demonstrates that all the H. saimiri-HTLV-1-X cell lines tested express active p42$^{tax}$.

TABLE 1

Tax Activity In H. Saimiri-HTLV-1 Transformed Cell Lines[a]

| Cell Line | % Conversion | | Ratio[b] |
|---|---|---|---|
| | pU3R1-CAT | pRSV-CAT | |
| Jurkat | 0.3 | 1.9 | 0.2 |
| ThyHUT[c] | 76.5 | 0.8 | 96 |
| Thy-1[d] | 76.7 | 3.0 | 25 |
| Thy-38[e] | 89.0 | 2.2 | 40 |
| Thy-40[d] | 76.2 | 1.9 | 40 |
| Kati-40[f] | 89.8 | 2.0 | 45 |

[a] $5 \times 10^6$ cells were transfected with 2 μg of the appropriate plasmid using DEAE-dextran, 48 hours post-transfection, the cells were counted, lysed, and $4 \times 10^3$ live cell equivalents were assayed for chloramphenicon acetyl transferase activity. Results represent percentage conversion to the acetylated form of chloramphenicol after a 15 minute enzymatic assay.
[b] pU3R1-CAT activity/pRSV-CAT activity.
[c] Thymocyte line derived from cocultivation with mitomycin-C treated HUT102 as described (see FIG. 3).
[d] $4 \times 10^4$ live cell equivalents were assayed for these cell lines.
[e] $10^5$ live cell equivalents were assayed for this cell line.
[f] Cord blood lymphocyte line (see FIG. 4).

In order to determine whether the cell populations were dependent on IL-2 the cultures were also split and a portion maintained in the same medium lacking IL-2. None of the cultures remained viable for more than 10 days in the absence of IL-2. The IL-2 dependence of the immortalized clones may reflect properties of the target cells utilized or the culture condition used as other cells transformed by HTLV-1 often result in a mixture of IL-2 independent and dependent clones.

The transformation to continuous IL-2 dependent growth appears to be a property of the HTLV-1-X region gene products as neither the intact H. saimiri virus nor the S4 deleted virus transforms human cells. Moreover, the non-human primate cells transformed by H. saimiri are a estricted CD8+/CD4− lymphocyte subpopulation. However, the H. saimiri vector permits the development of a immortal cell line that can be grown in the absence of other cells in contrast to the thymocyte and cord blood cell lines that must be co-cultivated with an HTLV-1 transformed cell line.

The predominance of unspliced versus spliced X region messenger RNA in the cell lines, suggests that the p27$^{rex}$ protein is functional, thus permitting the accumulation of unspliced RNAs. The similarity in the amount of HTLV-1X region RNA and protein despite differences in DNA copy number in various cells transformed by the *H. saimiri*-HTLV-1X vectors and by co-cultivation with HTLV-1 cells may reflect a comparatively high transcription rate for the HTLV-1 LTR in the presence of p42$^{tax}$ or may represent a limit of X-region RNA and protein expression tolerated by T-cells transformed with the *H. saimiri*-HTLV-1 X vectors.

It is evident that those skilled in the art given the benefit of the foregoing disclosure may make numerous modifications thereof and departures from the specific embodiments described herein without departing from the inventive concepts, and the present invention is to be limited solely by the scope and spirit of the appended claims.

We claim:

1. A vector consisting essentially of:
    (a) an *H. saimiri* genomic sequence having a deletion of the first 4.5 kbp of L-DNA at the left H-L-DNA border; and
    (b) an HTLV-1 or HTLV-2 3' LTR and a promoter operably linked to the HTLV-1 or HTLV-2 tax and rex genes.

2. The vector of claim 1, wherein the promoter is 5' to the initiation codon of the tax and rex genes.

3. The vector of claim 2, wherein the promoter is the LTR of the murine retrovirus SL3-3.

4. The vector of claim 3, wherein (b) includes nucleotides 5013 to 5694 and 6518 to 9054 of HTLV-1.

5. The vector of claim 1, wherein (b) includes 1011 nucleotides in the 3' portion of HTLV-2.

6. The vector of claim 1, wherein the *H. saimiri* genome is *H. saimiri* strain 11 S4 variant.

7. A vector capable of immortalizing a human CD4+/CD8− T-cell consisting essentially of:
    (a) an *H. saimiri* strain 11 S4 variant genomic sequence having a deletion of the first 4.5 kbp of L-DNA at the left H-L-DNA border; and
    (b) an HTLV-1 3' LTR and a promoter operably linked to the HTLV-1 tax and rex genes.

8. A method of transforming human CD4+/CD8− T-cell lines susceptible to *H. saimiri* infection comprising:
    (a) transfecting the CD4+/CD8− T-cell lines with the vector of claim 1, to transform the cell lines, and
    (b) culturing the transformed cell line.

9. The method of claim 8, wherein the transformed cell line is a human CD4+/CD8− T-lymphocyte cell line.

10. The method of claim 8, wherein the transformed cell line is a human leukemia CD4+/CD8− T-cell line.

11. An immortal cell line of human CD4+/CD8− T-lymphocytes that can be cultivated without the presence of feeder cells, comprising human T-lymphocytes transformed by the vector of claim 1.

12. An immortal cell line of human CD4+/CD8− T-lymphocytes that can be cultivated without the presence of feeder cells, comprising human T-lymphocytes transformed with the vector of claim 7.

13. A method of producing a desired protein which comprises transfecting the transformed cell line of claim 11 with a vector containing a heterologous gene for the desired protein under the control of a promoter responsive to the tax gene product, and culturing the transformed cell.

14. The method of claim 13, wherein the transformed cell line is a human T-lymphocyte cell line.

15. The method of claim 13, wherein the desired protein is chloramphenicol acetyltransferase.

16. A method of producing a desired protein which comprises transfecting the transformed cell line of claim 12 with a vector containing a heterologous gene for the desired protein under the control of a promoter responsive to the tax gene product, and culturing the transformed cell.

* * * * *